(12) United States Patent
Coffin et al.

(10) Patent No.: US 8,131,473 B1
(45) Date of Patent: Mar. 6, 2012

(54) DATA ANALYSIS METHODS FOR LOCATING ENTITIES OF INTEREST WITHIN LARGE, MULTIVARIABLE DATASETS

(75) Inventors: Marie Coffin, Cary, NC (US); Keith D. Allen, Cary, NC (US); Brian R. Bullard, Las Cruces, NM (US); Alan J. Higgins, Chapel Hill, NC (US)

(73) Assignee: Metabolon, Inc., Durham, NC (US)

( * ) Notice: Subject to any disclaimer, the term of this patent is extended or adjusted under 35 U.S.C. 154(b) by 1283 days.

(21) Appl. No.: 11/133,953

(22) Filed: May 20, 2005

Related U.S. Application Data

(60) Provisional application No. 60/572,844, filed on May 20, 2004.

(51) Int. Cl.
*G01N 33/48* (2006.01)
(52) U.S. Cl. .......................................................... 702/19
(58) Field of Classification Search .................... 702/19
See application file for complete search history.

(56) References Cited

U.S. PATENT DOCUMENTS

| | | | | |
|---|---|---|---|---|
| 6,059,724 A | * | 5/2000 | Campell et al. | 600/300 |
| 2007/0027634 A1 | * | 2/2007 | Mendrick et al. | 702/20 |

OTHER PUBLICATIONS

Haenen et al., "Utility of Rat Liver Slices to Estimate Hepatic Clearance for Application in Physiologically Based Pharmacokinetic Modeling: A Study with Tolbutamide, a Compound with Low Extraction Efficiency," Drug Metabolism and Disposition (2002) vol. 30, No. 3, pp. 307-313.*

Byczkowski et al., "A Biologically Based Pharamacodynamic Model for Liqid Peroxidation Stimulated by Trichloroethylene in Vitro", J. Biochem. Moelcular Toxicology (1999) vol. 13, No. 3/4, pp. 205-214.*

Zheng et al. "Proposed Modifications to Metabolic Model for Glycogen-Accumulating Organisms Under Anaerobic Conditions," Biotechnology and Bioengineering (2002) vol. 80, No. 3, pp. 277-279.*

Kriete et al. "Combined Histomorphometric and Gene-Expression Profiling Applied to Toxicology," Genome Biology, vol. 4, Issue 5 (Apr. 30, 2003).

* cited by examiner

*Primary Examiner* — Jerry Lin
(74) *Attorney, Agent, or Firm* — Jenkins, Wilson, Taylor & Hunt, P.A.

(57) ABSTRACT

The present invention provides data analysis methods for the rapid location of subsets of large, multivariable biological datasets that are of most interest for further analysis, for the investigation of molecular modes of action of biological phenomena of interest, and for the identification of sets of data points that best distinguish between experimental groups in larger datasets as putative biomarkers. While existing methods for analyzing large biological datasets generally provide too much information to the user, or not enough, the methods of the present invention entail taking user input on what kinds of trends are of interest and then finding results that match the designated trend. In such manner, the methods of the invention allow a user to quickly pinpoint the subset of data of most interest without a concomitant loss of a large percentage of relevant information, as is typical with standard methods. The methods of the invention allow for identification of molecular entities that are involved in a biological phenomenon of interest, entities that may have otherwise gone undiscovered in a large, multivariable dataset.

17 Claims, 7 Drawing Sheets
(7 of 7 Drawing Sheet(s) Filed in Color)

DATA ANALYSIS METHODS FOR LOCATING ENTITIES OF INTEREST WITHIN LARGE, MULTIVARIABLE DATASETS

CROSS REFERENCE TO RELATED APPLICATION

This application claims the benefit of, and incorporates herein by reference in its entirety, U.S. Provisional Application No. 60/572,844, filed May 20, 2004.

FIELD OF THE INVENTION

The present invention relates to data analysis methods for locating entities that are associated with a trend of interest in a dataset, in particular, entities such as genes, compounds and proteins. Useful applications of the invention include identification of a subset of data that is of most interest for further analysis and identification of a subset of data that best distinguishes between experimental groups.

BACKGROUND OF THE INVENTION

Recent advances in biological experimental techniques have resulted in a dramatic increase in the complexity and quantity of data that is being generated and the technology for generating data has outpaced the technology for helping scientists comprehend the new information contained in the data. For example, gene expression profiling, metabolic profiling, protein expression profiling and automated cell imaging techniques have created an explosion of data that is difficult to interpret, as the number of variables being measured and the sheer quantity of data generated renders manual analysis impractical if not impossible.

Given a large set of measurements on compounds, genes, proteins, etc., it is challenging to locate the subset of most interest in a particular experiment. Several statistical methods exist for analyzing such data that include examining the measurements one at a time and choosing all of the measurements that are statistically significant, using discriminant analysis (or some other classification procedure) alone to choose the set of measurements that distinguish between experimental groups, and using prior knowledge of the treatment mechanism to look for expected and inferred perturbations. None of the foregoing methods are fully effective in that they generally provide too much information to the user, or not enough.

The present invention addresses the problems associated with the analysis of complex datasets by providing methods that enable identification of a subset of data within a larger dataset that is of most interest for further analysis and identification of a subset of data that best distinguishes between experimental groups. Useful applications of the present invention include the discovery of biomarkers, disease targets and mode of action, and therapeutic chemical entities.

SUMMARY OF THE INVENTION

The present invention provides data analysis methods for the rapid location of subsets of large, multivariable biological datasets that are of most interest for further analysis, for the investigation of molecular modes of action of biological phenomena of interest, and for the identification of sets of data points that best distinguish between experimental groups in larger datasets as putative biomarkers. While existing methods for analyzing large biological datasets generally provide too much information to the user, or not enough, the methods of the present invention entail taking user input on what kinds of trends are of interest and then finding results that match the designated trend. In such manner, the methods of the invention allow a user to quickly pinpoint the subset of data of most interest without a concomitant loss of a large percentage of relevant information, as is typical with standard methods. The methods of the invention allow for identification of molecular entities that are involved in a biological phenomenon of interest, entities that may have otherwise gone undiscovered in a large, multivariable dataset.

Another advantage of the present invention is that it enables identification of a subset of data points that is indicative of a trend associated with a biological phenomenon of interest when the trend is not evident in a target dataset as a whole. In one case the trend is a known or predicted trend although it is not obvious in the target dataset. In another case the trend is evident in a dataset from one or more tissues, but not in the target tissue dataset. Thus, in one aspect, the methods of the invention enable identification as a biomarker a set of data points that correspond to chemical entities whose relative presence in a target tissue is potentially indicative of a biological phenomenon taking place in another less accessible tissue.

In one embodiment, the present invention provides data analysis methods for locating subsets of complex biological datasets that are of most interest for further analysis. The methods of the invention comprise the steps of: a) obtaining a set of data points for a biological phenomenon of interest; b) designating a trend in the set of data that is associated with the biological phenomenon of interest; c) developing a mathematical model of the trend; and d) testing each data point in the set for adherence to the mathematical model, wherein the data points adhering to the model are the subset of most interest for further analysis. In the methods of the invention, the designated trend may be observable in a display of the dataset as a whole or may instead be a known trend or a trend that is predicted to be associated with the biological phenomenon of interest.

In another embodiment, the invention provides data analysis methods for investigating the molecular mode of action of a biological phenomenon of interest. The methods comprise the steps of: a) obtaining biochemical profiling, gene expression profiling, or protein expression profiling data for a biological phenomenon of interest; b) designating a trend in the data that is associated with the biological phenomenon; c) developing a mathematical model of the trend; d) testing each data point in the set for adherence to the mathematical model; and e) identifying one or more metabolic pathways to which the data points that adhere to the model belong, wherein the mode of action of the phenomenon of interest affects the identified metabolic pathways. In the methods of the invention, the designated trend may be observable in a display of the dataset as a whole or may instead be a known trend or a trend that is predicted to be associated with the biological phenomenon of interest.

In a further embodiment, the invention provides data analysis methods for locating a set of biological data points as a biomarker of a trend associated with a biological phenomenon of interest. The methods comprise the steps of: a) obtaining a dataset for a biological phenomenon of interest in one or more tissues that include a target tissue; b) designating a trend in the dataset that is associated with the biological phenomenon of interest for one of the tissues; c) developing a mathematical model of the trend; d) testing each data point of the one tissue dataset for adherence to the mathematical model; e) processing the data points that adhere to the mathematical model using stepwise discriminant analysis (SDA) to identify a small group of the adhering data points that best distinguishes between the experimental groups of the one dataset, wherein the small group i) consists of the data points rated most highly by the SDA, ii) each of the data points in the small group varies significantly from the baseline in the one dataset, and iii) if the small group is not derived from the target tissue, each of the data points in the small group is detectable in the target tissue and varies significantly from the baseline in the target tissue dataset; and, optionally, f) performing parametric discriminant analysis on the small group to obtain a discrimination score that measures how well the small group distinguishes between the experimental groups of the one dataset, wherein the higher the discrimination score the better the indication of the small group as a putative biomarker in the target tissue of the trend of interest. In the methods of the invention, the designated trend may be observable in a display of the dataset as a whole or may instead be a known trend or a trend that is predicted to be associated with the biological phenomenon of interest. In a particular embodiment of the invention, the trend of interest is designated in a tissue other than the target tissue, and the discriminating small group is indicated as a putative biomarker in the target tissue.

In other embodiments of the invention, sets of data points that correspond to groups of biochemical metabolites that best distinguish between experimental groups, are provided for use as early biomarkers in serum and/or urine of liver damage and/or disease.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
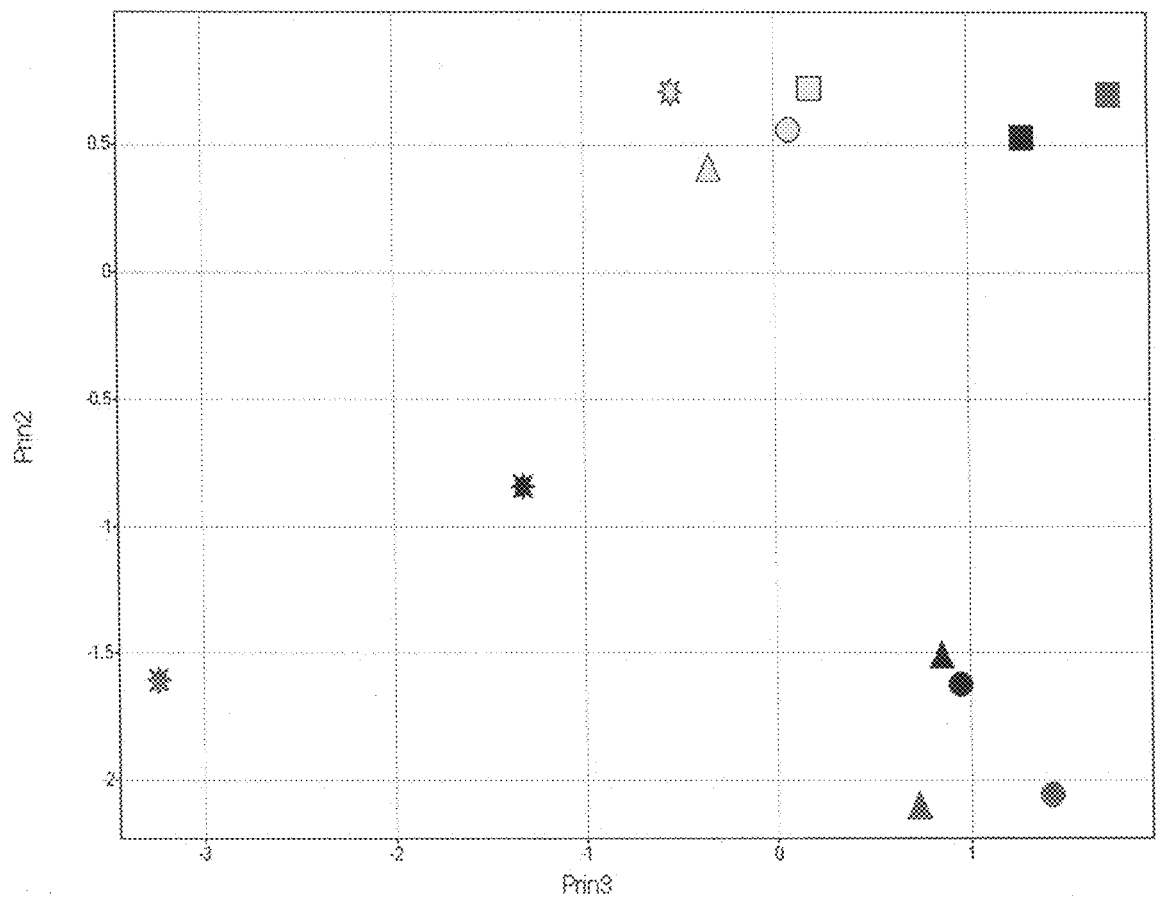
FIG. 1. Principal component analysis (PCA) of rat liver biochemical profiling data collected for a study of acetaminophen-induced liver toxicity. Rats administered a single dose of acetaminophen (APAP) at 150, 1500 or 2000 mg/kg p.o. were sacrificed at 6, 18, 24, or 48 hr post dosing (6 rats per group). The 150 mg/kg dose is equivalent to a low overdose level in humans (~40 g) and 1500 mg/kg is a low toxic dose in rats. Livers of the rats were processed for biochemical profiling data and the third principal component (x-axis) is plotted against the second principal component (y-axis) for each of the 6, 18, 24 and 48 hr time points at 150 mg/kg (yellow), 1500 mg/kg (black), and 2000 mg/kg (green) concentrations of acetaminophen. Each data point represents the average for six animals.

The present invention addresses the problems associated with the analysis of large, multivariable datasets by providing methods that enable identification of a subset of data points within a dataset that is of most interest for further analysis and identification of a small group of data points that best distinguishes between experimental groups. Useful applications of the present invention include the discovery of biomarkers, disease targets and mode of action, and therapeutic chemical entities.

Given a large set of measurements on compounds, genes, proteins, etc., it is challenging to locate the subset of most interest in a particular experiment. Several statistical methods exist for analyzing such data that include: 1) Examining the measurements one at a time and choosing all of the measurements that are statistically significant. This method is too general in that it fails to distinguish between results that are relevant to the issue being studied and those that are not relevant to the particular issue. 2) Using discriminant analysis (or some other classification procedure) alone to choose the set of measurements that distinguish between experimental groups. This method is also too general because some experimental groups may, in fact, not be greatly affected by the experiment. Attempting to distinguish these groups from each other causes the method to include many measurements that are irrelevant to the problem. 3) Using prior knowledge of the treatment mechanism or disease mechanism to look for expected and inferred perturbations of individual molecules or entities. This method is too specific, as it only looks for what is expected and will not lead to new discoveries, except in the negative sense. Thus, existing methods generally provide too much information to the user, or not enough.

The data analysis methods of the present invention address each of the foregoing problems by using more information than the other methods, in the form of user input on what kinds of trends are of interest for a particular dataset. Once a trend has been designated for a dataset, the methods of the invention enable location of a subset of the data points that corresponds to particular molecular entities that match the designated trend. In this manner, one or more molecules are discovered to be associated with a biological phenomenon even though the trend for the particular molecule(s) may not have been evident in the dataset as a whole. The methods of the invention allow for identification of molecular entities that are involved in a biological phenomenon of interest, entities that may have otherwise gone undiscovered in a complex dataset.

In one embodiment, the present invention provides data analysis methods for the rapid location of subsets of complex biological datasets that are of most interest for further analysis. The biological datasets of the invention include, but are not limited to; data obtained or collected using well known techniques such as biochemical profiling, gene expression profiling, and protein expression profiling, as well as other techniques such as tissue feature analysis. Tissue feature analysis refers to quantitative tissue image analysis of structural features in tissue elements using digital microscopy to generate data that objectively describes tissue phenotype, with the potential for detection of subtle changes that are undetectable to the human eye as described, for example, in Kriete et al., 4 *Genome Biology* R32.1-0.9 (2003). The datasets for analysis using the methods of the invention comprise a baseline and one or more experimental groups. The methods of the invention allow a user to quickly pinpoint the subset of data of most interest without a concomitant loss of a large percentage of relevant information, as is typical with standard methods. In related embodiments described in more complete detail below, the invention provides data analysis methods for investigating the molecular mode of action of a biological phenomenon of interest and for identifying data points that best distinguish between experimental groups for use as biomarkers. In one aspect the invention is particularly useful for the identification and use of small molecule biomarkers of disease and/or toxicity, disease staging, target identification/validation, and monitoring of drug efficacy/toxicity.

In one embodiment of the present invention, a subset of data points is identified that correspond to a trend associated with a biological phenomenon of interest when the trend is evident through visual inspection of the dataset as a whole. Visual inspection of the dataset as a whole includes inspection of the dataset prior to or subsequent to the data being reduced or otherwise manipulated, such as for example, through use of a two-dimensional plot of a first principal component vs. a second principal component, or other representation. In another aspect of the embodiment, a subset of data points is identified that corresponds to a trend associated with a biological phenomenon of interest when the trend is not evident by visual inspection of the dataset as a whole, even after data reduction or other manipulation. In this case, the trend is designated because it is a known or predicted trend for the biological phenomenon of interest even though the trend is not evident in the dataset as a whole. A related embodiment is when the trend of interest is evident in another dataset, for example a dataset from another tissue, but the trend is not evident in the dataset for the tissue being targeted.

Thus, in one embodiment, the present invention provides data analysis methods for locating subsets of large, multivariable biological datasets that are of most interest for further analysis. The methods of the invention comprise the steps of: a) obtaining a set of data points for a biological phenomenon of interest wherein the set of data points comprises a baseline and one or more experimental groups; b) designating a trend in the set of data that is associated with the biological phenomenon of interest; c) developing a mathematical model of the trend; and d) testing each data point in the set for adherence to the mathematical model, wherein the data points adhering to the model are the subset of most interest for further analysis. In the methods of the invention, the designated trend may be observable in a display of the dataset as a whole or may instead be a known trend or a trend that is predicted to be associated with the biological phenomenon of interest even if it is not evident in the dataset as a whole. In preferred embodiments of the invention, the sets of data points comprise biochemical profiling data, gene expression profiling data, protein expression profiling data, and tissue feature data.

In another embodiment, the invention provides data analysis methods for investigating the molecular mode of action of a biological phenomenon of interest. The methods comprise the steps of: a) obtaining biochemical profiling data, gene expression profiling data, protein expression profiling data, or tissue feature data for a biological phenomenon of interest, wherein the data comprises a baseline and one or more experimental groups; b) designating a trend in the data that is associated with the biological phenomenon; c) developing a mathematical model of the trend; d) testing each data point in the set for adherence to the mathematical model; and e) identifying one or more metabolic pathways to which the data points that adhere to the model belong, wherein the mode of action of the phenomenon of interest affects the identified metabolic pathways. In the methods of the invention, the designated trend may be observable in a display of the dataset as a whole or may instead be a known trend or a trend that is predicted to be associated with the biological phenomenon of interest, even if it is not evident in the dataset as a whole.

Another embodiment of the invention is directed to identification of subsets of data points that best distinguish between experimental groups as putative biomarkers. The invention provides data analysis methods for locating a set of biological data points as a biomarker of a biological phenomenon of interest. The biomarkers of the invention have a range of uses including biomarkers of disease and/or toxicity, disease staging, target identification/validation, and monitoring of drug efficacy/toxicity. In a particular aspect of this embodiment, the methods of the invention are useful for identifying a subset of data points corresponding to molecular entities as a putative biomarker, wherein the relative presence of the subset of data points in a target tissue is potentially indicative of a biological phenomenon taking place in another less accessible tissue.

Thus, the methods of the invention are directed to identification of subsets of data points that best distinguish between experimental groups as putative biomarkers and the methods comprise the steps of a) obtaining a dataset for a biological phenomenon of interest in one or more tissues that include a target tissue, wherein the dataset comprises a baseline and one or more experimental groups; b) designating a trend in the dataset that is associated with the biological phenomenon of interest for one of the tissues; c) developing a mathematical model of the trend; d) testing each data point of the one tissue dataset for adherence to the mathematical model; e) processing the data points that adhere to the mathematical model using stepwise discriminant analysis (SDA) to identify a small group of the adhering data points that best distinguishes between the experimental groups of the one dataset, wherein the small group i) consists of the data points rated most highly by the SDA, ii) each of the data points in the small group varies significantly from the baseline in the one dataset, and iii) if the small group is not derived from the target tissue, each of the data points in the small group is detectable in the target tissue and varies significantly from the baseline in the target tissue dataset; and, optionally, 0 performing parametric discriminant analysis on the small group to obtain a discrimination score that measures how well the small group distinguishes between the experimental groups of the one dataset, wherein the higher the discrimination score the better the indication of the small group as a putative biomarker in the target tissue for the biological phenomenon of interest. In preferred embodiments of the invention, the datasets comprise biochemical profiling data, gene expression profiling data, protein expression profiling data, and tissue feature data.

In a particular instance of the foregoing embodiment the one tissue and the target tissue are the same, such that the dataset for which the biological phenomenon of interest is obtained is for the target tissue. The target tissues of the invention are preferably those tissues that are most readily attainable in humans and animals, for example, tissues such as serum and blood, although the methods of the invention do not restrict any tissue from serving as a target tissue. Similar to the methods for locating subsets of most interest for further analysis and for investigating modes of action, the methods of the invention for discovering biomarkers also encompass designating a trend in the dataset for the target tissue that is either observable in a display of the dataset as a whole or instead is a known trend or a trend that is predicted to be associated with the biological phenomenon of interest. Optionally, parametric discriminant analysis is performed on the small group to obtain a discrimination score that measures how well the small group distinguishes between the experimental groups of the dataset. The higher the discrimination score the better the indication for the small group as a putative biomarker in the target tissue for the biological phenomenon of interest.

In another instance of the foregoing embodiment the trend of interest is designated in a tissue other than the target tissue, and the discriminating small group is indicated as a putative biomarker in the target tissue. The one tissue and the target tissue are not the same in this embodiment of the invention. Because the discriminating small group is identified in a tissue other than the target tissue, each of the data points in the small group must meet the criterion (iii) noted above of being detectable in and varying significantly from baseline in the target tissue in addition to the criteria of being rated most highly by the SDA and varying significantly from the baseline in the originating non-target dataset. Similar to that described for the previous embodiments, the designated trend in the non-target dataset is either observable in a display of the dataset as a whole or instead is a known trend or a trend that is predicted to be associated with the biological phenomenon of interest. Optionally, parametric discriminant analysis is performed on the small group to obtain a discrimination score that measures how well the small group distinguishes between the experimental groups of the target dataset. The higher the discrimination score the better the indication for the small group as a putative biomarker in the target tissue for the biological phenomenon of interest. Using the methods of the invention in this manner allows for identification of putative biomarkers that are measurable in readily accessible target tissues, biomarkers that might not otherwise be discoverable through sole analysis of data derived from the target tissue.

In another embodiment of the invention, a putative biomarker suite is provided for early detection and monitoring of liver damage and or disease in serum and/or urine. Twenty four chemical entities for which a combined relative response in liver, serum and urine is indicative of liver damage/toxicity are listed in Table III. The relative response of the foregoing biochemical metabolites, measured according to the methods of the invention, is indicative of liver damage and, thus, useful as a non-invasive biomarker for the early detection/diagnosis of liver toxicity and/or disease. Measurement of relative response in serum or urine for any combination of one or more of the response peaks listed in Table III may also be useful as an early biomarker of liver damage and/or disease. The combinations of response peaks having the highest explanatory power of the observed trend and statistically significant changes among dose/time groups in the target tissue are the preferred combinations for biomarker use. In the methods of the invention, response relative to control is measured, for example, by use of gas or liquid chromatography followed by mass spectrometry. However, any technique for quantifying metabolite response relative to control, known to those of ordinary skill in the art, is applicable to the methods of the present invention.

In another embodiment of the invention, a biomarker suite in urine is provided for early detection and monitoring of liver damage and or disease. Six chemical entities for which a combined relative response in urine is indicative of liver damage/toxicity are listed in Table IV with the exception of Peak13, and are as follows: aspartic acid, Peak12, L-glutamine, Peak20, succinic acid, and Peak26. The relative response in urine of the foregoing biochemical metabolites, measured according to the methods of the invention, are indicative of liver damage and, thus, useful as a non-invasive biomarker for the early detection/diagnosis of liver toxicity and/or disease. In one aspect of the invention, liver damage/disease is indicated by measurement in urine of a standard difference in response relative to control of greater than or equal to 2 for each of the above listed metabolites. The response relative to control in urine for metabolites, L-glutamine and Peak20, is a positive response that is greater than or equal to 2, whereas the relative response for aspartic acid, Peak12, succinic acid, and Peak26 is a negative response of greater than or equal to 2 relative to control. Response relative to control is measured, for example, by use of gas or liquid chromatography followed by mass spectrometry. However, any technique for quantifying metabolite response relative to control, known to those of ordinary skill in the art, is applicable to the methods of the present invention. The following examples are offered by way of illustration and not by way of limitation.

EXPERIMENTAL

Example 1

Acetaminophen-Induced Liver Toxicity Study
Design and Data Acquisition

An acetaminophen-induced liver toxicity study was performed as follows. Rats were administered a single dose of acetaminophen (APAP) at 0, 50, 150, 1500 or 2000 mg/kg p.o. (6 rats per group). The 150 mg/kg dose is equivalent to a low overdose level in humans (~10 g) and 1500 mg/kg is a low toxic dose in rats. The rats were sacrificed at 6, 18, 24, and 48 hr post dosing. Livers of the rats were processed for biochemical profiling, histopathology and gene expression analysis. For the 0, 50 and 1500 mg/kg dose groups, rat urine was collected at −24-0, 0-6, 6-24, and 24-48 hr relative to dosing. Similarly, rat serum was collected at 48 hr for the 0, 50 and 1500 mg/kg groups.

Sample Preparation

Rat tissue was prepared for LC-MS analysis as follows. Rat liver tissue samples were frozen upon collection. A slice of each frozen sample was placed into a mortar, covered with liquid nitrogen, and ground with a pestle. 100 mg of ground sample was placed in a cryovial, extraction fluid and beads were added, and the sample was further ground and then centrifuged. The supernatant was transferred to a clean cryovial, centrifuged again, and then transferred to a well of a 96-well plate.

Rat biofluids were prepared for LC-MS analysis as follows. Rat urine and serum samples were vortexed. An aliquot of 500 µL was transferred to a clean cryovial and centrifuged. The supernatant was transferred to a clean cryovial and centrifuged again. The supernatant was transferred to another clean cryovial and diluted 4:1 with extraction solvent. An aliquot of 100 µL was transferred to a well of a 96-well plate.

LC-MS Analysis

LC-MS analysis of the rat tissue and biofluid samples was performed on an Applied Biosystems Mariner liquid chromatograph coupled with a time of flight mass spectrometer (LC-TOF). The mass resolution for the mass spectrometer employed in this experiment was 0.200 amu. One LC was employed with a splitter that allowed for the eluent to be delivered to two TOF MS instruments, one operating in positive ionization mode, the other in negative ionization mode. Compounds detected by LC-MS with an electrospray ion source were cataloged based on retention times and mass-to-charge ratio (m/z) of the ions characteristic of each peak. Mass spectrometric data were collected from 80-900 amu. Raw LC-MS data were processed using the commercially available software TARGETDB (Thru-Put Systems, Inc., Orlando, Fla.).

RNA Isolation

Upon necropsy, liver tissue from left lateral lobe is cubed (0.5 cm or smaller) and stored in RNALATER (Ambion, Austin, Tex.) overnight at 4+/−3° C. then transferred to −20+/−10° C. until RNA isolation (within 60 days). RNA is isolated from approximately 130-150 mg tissue using RNEASY midi spin columns (Qiagen, Valencia, Calif.) according to the manufacturer's protocol. The RNA is concentrated using Millipore Microcon centrifugal filter devices (Billerica, Mass.).

RNA Labeling/Microarray Hybridization

One µg total RNA from either an individual rat or a pooled sample is amplified and labeled with a fluorophore (either Cy3 or Cy5) using Agilent Technologies' Low RNA Input Linear Amplification Labeling (Palo Alto, Calif.) following the manufacturer's protocol. The resulting fluorescently labeled cRNA is tested on a Nanodrop ND-100 spectrophotometer (Rockland, Del.) and an Agilent Bioanalyzer (Palo Alto, Calif.) to ensure proper quantity and quality. Equal amounts (750 ng) of Cy3-labeled cRNA from an individual rat and Cy5-labeled cRNA from the corresponding pooled control are hybridized to an Agilent Rat Oligo Array (Palo Alto, Calif.). In a second hybridization, the fluorophores used to label each sample are reversed. Therefore, two hybridizations are performed for each individual rat examined in this study.

Example 2

Data Analysis Methods: Locating a Subset of Most Interest that Corresponds to an Observed Trend A targeted list of relative responses for peaks and peaks annotated as known compounds was produced from the LC/MS data for the rat liver samples described in Example 1. The resulting biochemical profiling data was subjected to Principal Component Analysis (PCA), showing trends over both dose and time (see FIG. 1). The third principal component (x-axis) is plotted against the second principal component (y-axis) for each of the 6, 18, 24 and 48 hr time points for acetaminophen does 150 mg/kg (yellow), 1500 mg/kg (black), and 2000 mg/kg (green). Each data point represents the average for six animals.

Figure 2:
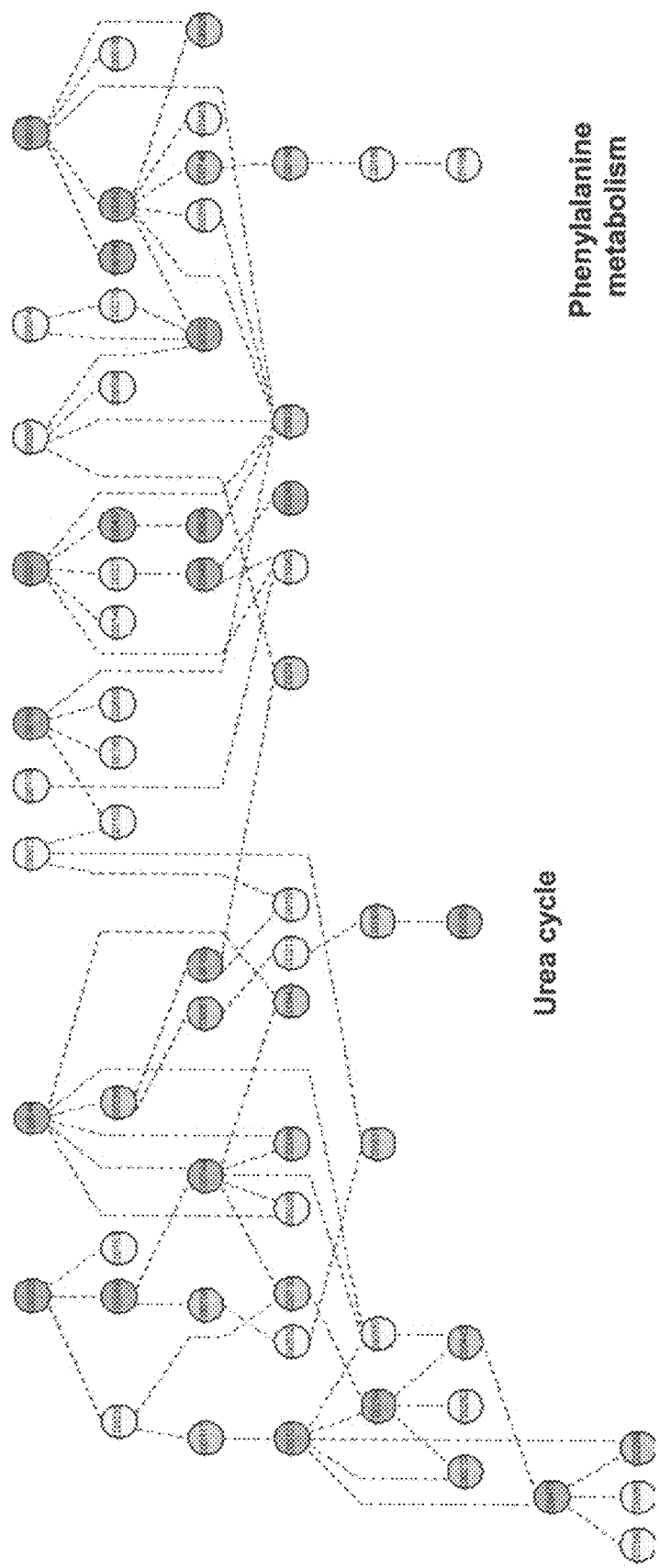
FIG. 2. A visualization of an identified subset of compounds whose relative responses follow trends observed for acetaminophen-induced changes in rat liver. The diagram displays that each of the identified compounds belongs to one of three interconnected metabolic pathways including purine metabolism, urea cycle and phenylalanine metabolism. In the diagram, a circle containing a KEGG compound identifier represents each of the compounds. The color red versus the color green represents whether the relative response of the compound increased or decreased in response to the acetaminophen-induced toxicity, respectively. Compounds that were not analyzed in the biochemical profiling study are designated as yellow circles. Compounds whose relative responses were not statistically different from control are in blue.

Mathematical models of the trends observed in the PCA plot were developed. Two trends were observed in the PCA plot. Trend 1 is a trend of increasing distance from control as the dose increases at any given time point. Trend 2 is a trend of change from one time point to the next that is in the same direction and of increasing magnitude as dose increases. Each of the relative response peaks in the liver biochemical profiling dataset was tested for adherence to the mathematical models to locate the subset of peaks that followed the observed trends. The peaks that adhered to the model were identified as the subset of most interest for further analysis of acetaminophen-induced liver changes and are listed in Table I. To further investigate the mode of action of acetaminophen, the known compounds in the identified subset were mapped to metabolic pathways. FIG. 2 is a diagram displaying that each of the identified compounds belongs to one of only three interconnected metabolic pathways, purine metabolism, urea cycle and phenylalanine metabolism. From this, it was hypothesized that the mode of action of acetaminophen toxicity affects these three adjacent pathways.

TABLE I

List of peaks located by trendFinder whose effect increases monotonically with dose.

| Compound Name |
| --- |
| L-tyrosine |
| N-acetylneuraminic acid |
| agmatine |
| glutathione oxidized |
| peak03 |
| peak05 |
| peak12 |
| peak13 |
| peak24 |
| phosphoethanolamine |
| 2-ketobutyric acid |
| 3,4-dihydroxyphenylalanine |
| L-histidine |
| L-ornithine |
| L-phenylalanine |
| N-acetyl-L-glutamate |
| argininosuccinic acid |
| beta-nicotinamide adenine dinucleotide |
| cytidine |
| peak10 |
| peak11 |
| peak16 |
| phenylpyruvate |
| phosphocreatine |
| phosphocreatine |
| ribose |
| 2,4-diamino-n-butyric Acid |
| 2-ketobutyric acid |
| 3,4-dihydroxyphenylalanine |
| GMP |
| L-cysteine |
| L-histidine |
| L-phenylalanine |
| L-proline |
| L-tyrosine |
| L-tyrosine |
| N-acetyl-L-glutamate |
| acetyl-L-carnitine |
| argininosuccinic acid |
| cystine |
| cytidine |
| gallic acid |
| guanosine |
| guanosine-5-triphosphate |
| hippuric acid |
| inosine |
| peak01 |
| peak07 |
| peak09 |
| peak11 |
| peak21 |
| phosphoenolpyruvate |
| phosphoethanolamine |
| ribose |
| 2-deoxyuridine |
| 2-ketobutyric acid |
| 3,4-dihydroxyphenylalanine |
| 3-hydroxyanthranillic acid |

TABLE I-continued

List of peaks located by trendFinder whose effect
increases monotonically with dose.

Compound Name

GMP
L-histidine
L-methionine
L-phenylalanine
L-tyrosine
L-tyrosine
N-acetyl-L-glutamate
allantoin
beta-nicotinamide adenine dinucleotide
cystathionine
cystine
diaminopimelic acid
peak01
peak11
peak16
peak26
phosphoethanolamine
ribose Example 3

Data Analysis Methods: Locating a Subset of Most
Interest that Corresponds to a Predicted Trend that is
not Evident in a Dataset as a Whole In this application of the invention, the targeted list of relative responses for peaks and peaks annotated as known compounds from Example 2 was analyzed to identify a subset that adhered to a predicted trend not evident in the dataset as a whole. The predicted trend of interest was a linear response across dose and a linear or quadratic response across time. Mathematical models representing the trend of interest were developed and each of the relative response peaks in the targeted list dataset was tested for adherence to the model. The subset of peaks that adhered to the designated trend is presented in Table II. Each of the compounds corresponding to the peaks in Table II is potentially implicated as having a role or being affected in acetaminophen induced liver toxicity.

TABLE II

Compounds associated with the mode of action
of acetaminophen toxicity.

Compound name 2-deoxyuridine
2-ketobutyric acid
3',5'-cyclic AMP
3,4-dihydroxyphenylalanine
GMP
L-asparagine
L-aspartate
L-citrulline
L-glutamine
L-histidine
L-lysine
L-ornithine
L-phenylalanine
L-serine
L-tyrosine
N-acetylneuraminic acid
argininosuccinic acid
beta-nicotinamide adenine dinucleotide
cystathionine
cysteic Acid TABLE II-continued Compounds associated with the mode of action
of acetaminophen toxicity.

Compound name cytidine-3'-monophosphate
glucosamine-6-phosphate
glutathione oxidized
guanosine-5'-diphosphate
guanosine-5-triphosphate
lactic acid
malic acid
nicotinamide
orotidine
pantothenic acid
peak03
peak07
peak08
peak11
peak12
peak13
peak16
peak18
peak19
peak20
peak21
peak24
peak25
peak26
phosphocreatine
pipecolic acid
pyruvic acid
raffinose
ribose
sarcosine
taurine
xanthine Example 4

Data Analysis Methods: Locating a Subset of Most
Interest that Corresponds to a Predicted Trend that is
not Evident in a Dataset as a Whole In this application of the invention, the mathematical model of Example 3 was modified to assume that the subjects would have shown zero difference from controls at time zero (this assumption is necessary because the subjects were not actually observed at time zero). As in Example 3, the predicted trend of interest was a linear response across dose and a linear or quadratic response across time, in addition to the assumption of a zero response at time zero. Mathematical models representing the foregoing trend of interest were developed. A subset of the relative response peaks in the targeted list dataset was extracted, namely those peaks that showed a significant difference from control at one or more doses and one or more timepoints. This subset was then tested for adherence to the mathematical model. The subset of peaks that adhered to the designated trend is presented in Table III. Each of the compounds corresponding to the peaks in Table III is potentially implicated as having a role or being affected in acetaminophen induced liver toxicity.

Figure 3:
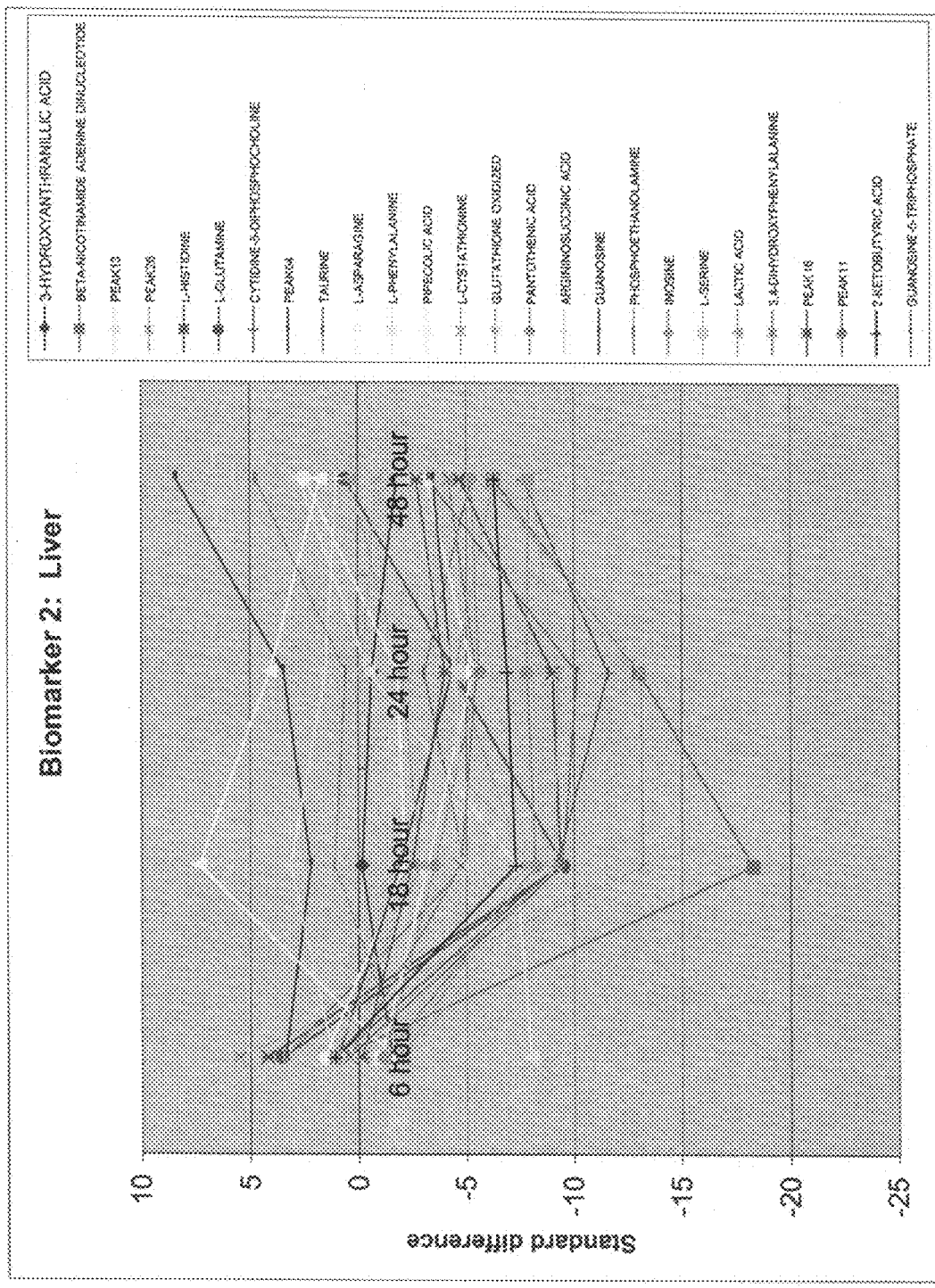
FIG. 3. A graph of response relative to control in liver (standard difference; y-axis) versus time from acetaminophen (2000 mg/kg) dosing (x-axis) for each of the 24 peaks listed in Table III.
Figure 4:
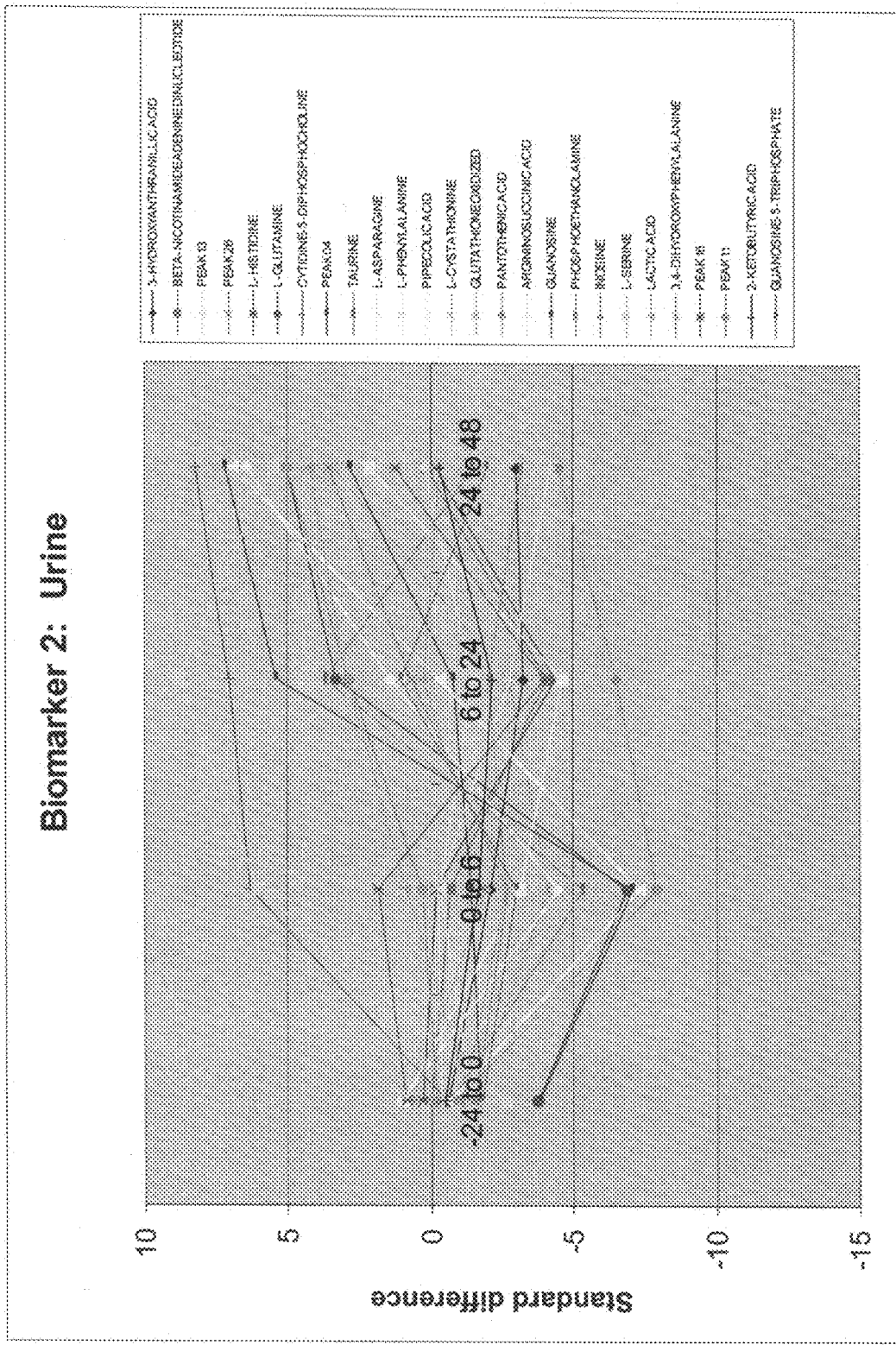
FIG. 4. A graph of response relative to control in urine (standard difference; y-axis) versus time from acetaminophen (1500 mg/kg) dosing (x-axis) for each of the 24 peaks listed in Table III.
Figure 5:
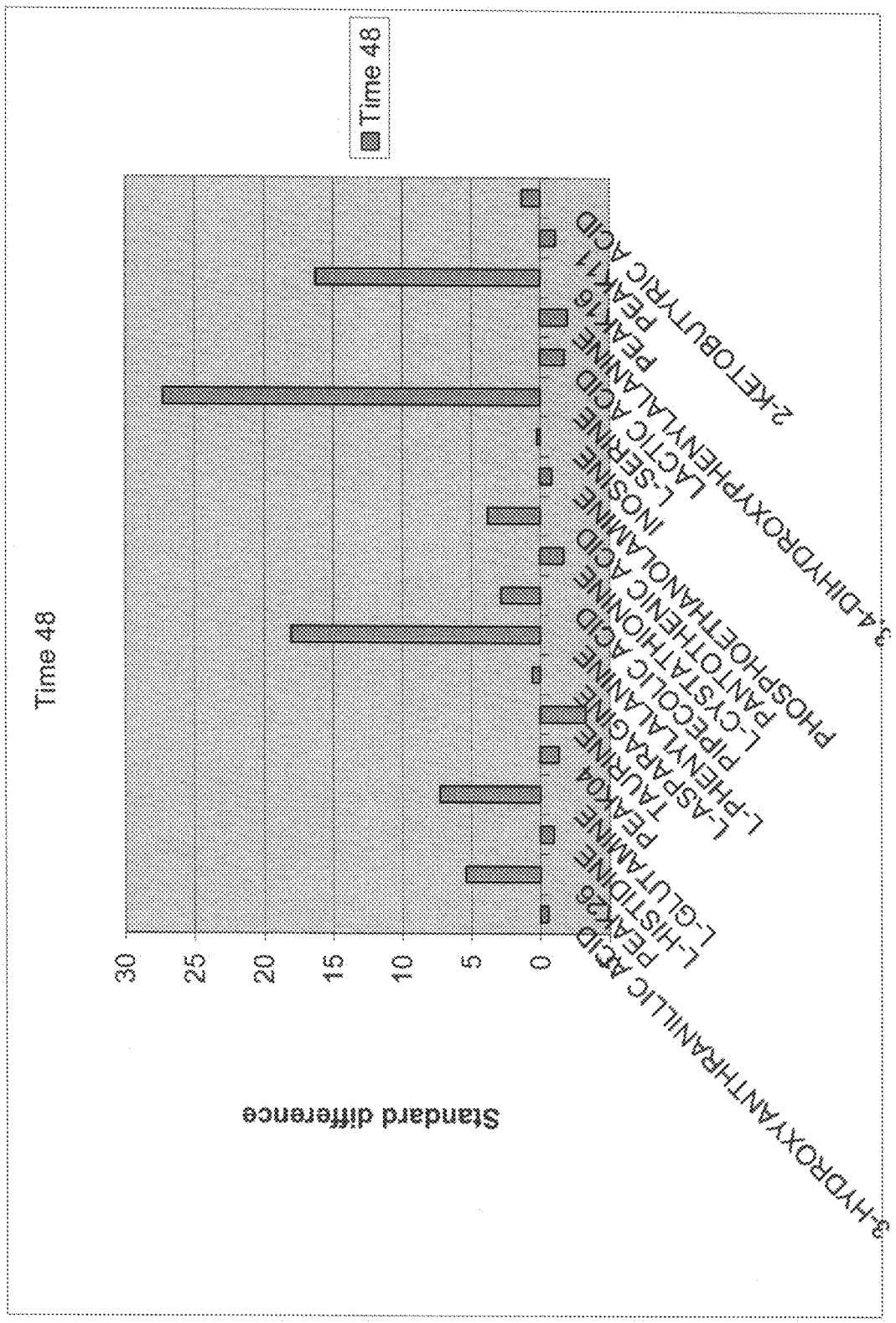
FIG. 5. A graph of response relative to control in serum (standard difference; y-axis) at 48 hours after acetaminophen (1500 mg/kg) dosing for each of the peaks listed in Table III (x-axis).

A graph of response relative to control in liver (standard difference; y-axis) versus time from acetaminophen (2000 mg/kg) dosing (x-axis) for each of the 24 peaks listed in Table III is shown in FIG. 3. Similarly, a graph of response relative to control in urine (standard difference; y-axis) versus time from acetaminophen (1500 mg/kg) dosing (x-axis) for each of the 24 peaks listed in Table III is shown in FIG. 4. FIG. 5 is a graph of response relative to control in serum (standard difference; y-axis) at 48 hours after acetaminophen (1500 mg/kg) dosing for each of the peaks listed in Table III (x-axis). Measurement of relative response in serum or urine for any combination of one or more of the response peaks listed in Table III may be useful as an early biomarker of liver damage and/or disease. The combinations of response peaks having the highest explanatory power of the observed trend and statistically significant changes among dose/time groups in the target tissue are the preferred combinations for biomarker use.

TABLE III

A biomarker suite of acetaminophen induced liver toxicity.

Compound

3-HYDROXYANTHRANILLIC ACID
BETA-NICOTINAMIDE ADENINE DINUCLEOTIDE
PEAK13
PEAK26
L-HISTIDINE
L-GLUTAMINE
CYTIDINE-5-DIPHOSPHOCHOLINE
PEAK04
TAURINE
L-ASPARAGINE
L-PHENYLALANINE
PIPECOLIC ACID
L-CYSTATHIONINE
GLUTATHIONE OXIDIZED
PANTOTHENIC ACID
ARGININOSUCCINIC ACID
GUANOSINE
PHOSPHOETHANOLAMINE
INOSINE
L-SERINE
LACTIC ACID
3,4-DIHYDROXYPHENYLALANINE
PEAK16
PEAK11
2-KETOBUTYRIC ACID
GUANOSINE-5-TRIPHOSPHATE

Example 5

Figure 6:
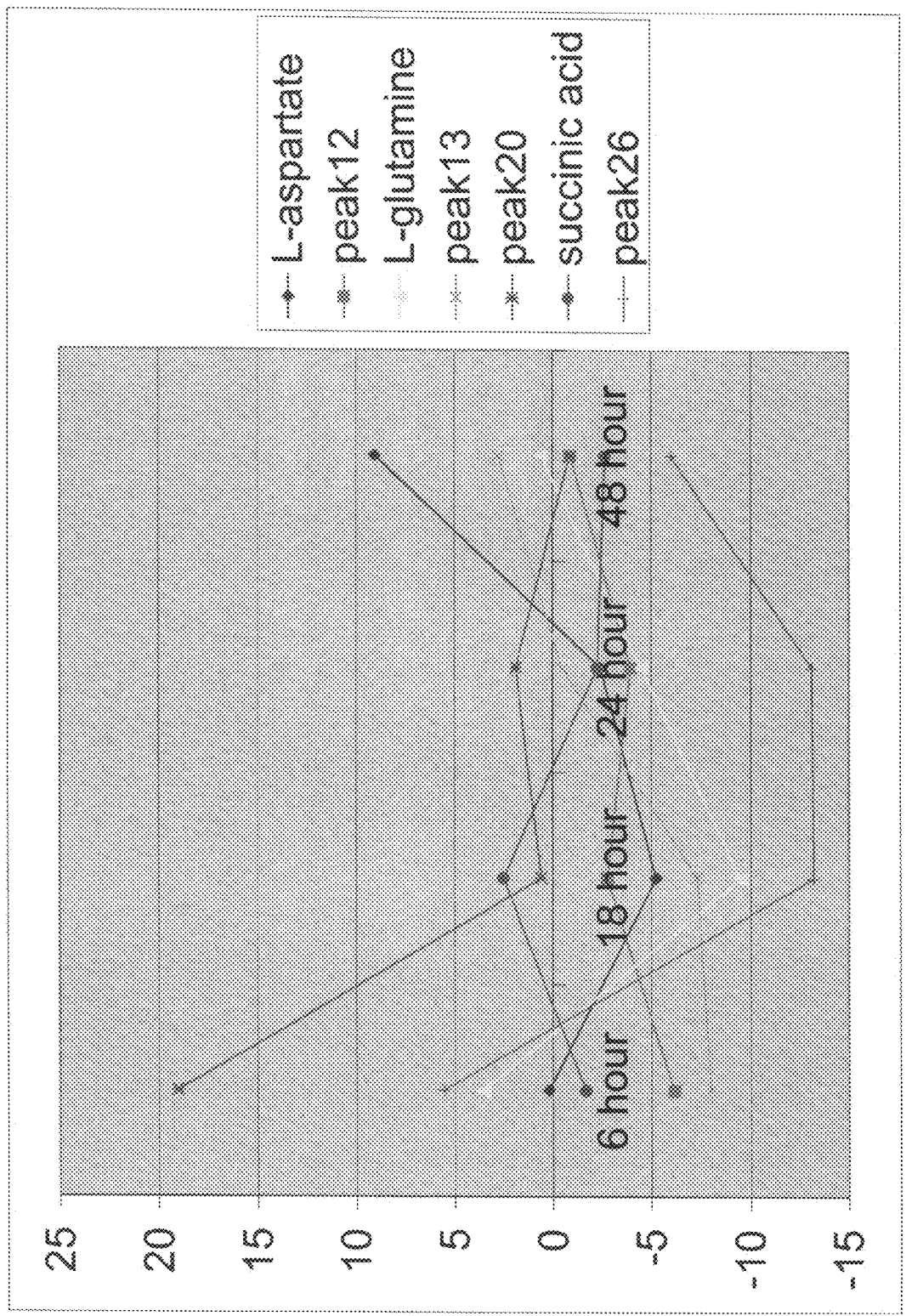
FIG. 6. A graph of response relative to control in liver tissue (standard difference; y-axis) versus time from acetaminophen (2000 mg/kg) dosing (x-axis) for each of the 7 peaks listed in Table IV.

Data Analysis Methods: Locating a Subset as a Putative Biomarker in a Target Tissue The subset of peaks identified for rat liver in Example 2 as being of most interest for investigation into acetaminophen induced liver damage (Table I) was further analyzed for an ability to act as a putative biomarker of acetaminophen toxicity in a target tissue such as serum or urine. In this application, stepwise discriminant analysis (SDA) was performed on the subset of relative response peak data points identified in liver to extract a relatively small group of the data points with highest explanatory power of the observed PCA plot trend and statistically significant changes among dose/time groups. The forgoing analysis resulted in the small group of 7 peaks/compounds that are listed in Table IV. Compounds corresponding to the 7 peaks listed in Table IV are hypothesized to be associated with acetaminophen liver toxicity. A graph of response relative to control (standard difference; y-axis) versus time from dosing (x-axis) for each of the 7 peaks in liver tissue is shown in FIG. 6.

TABLE IV

Putative biomarker suite.

Compound Name aspartic acid
Peak12
glutamine
Peak13
Peak20
succinic acid
Peak26

Figure 7:
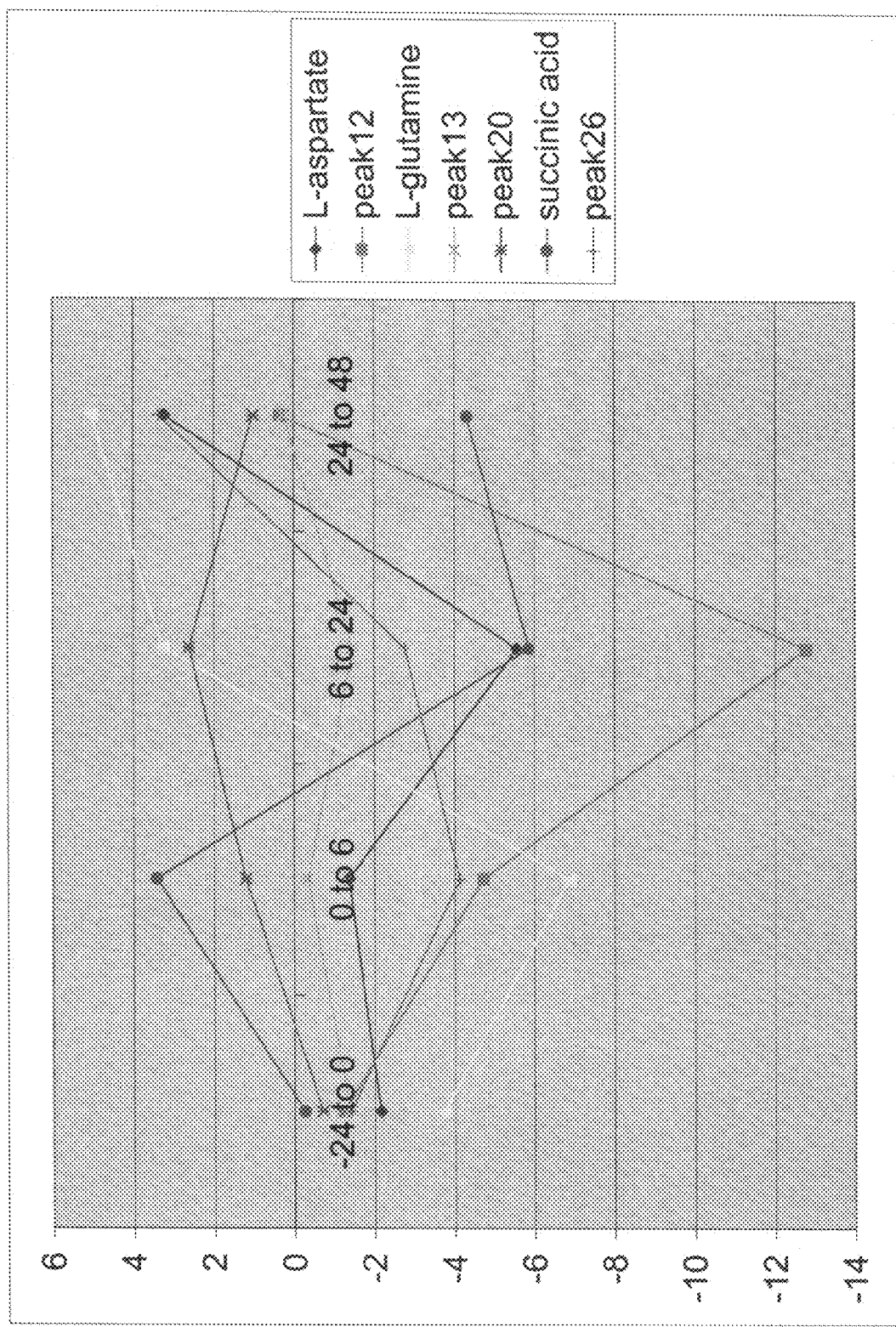
FIG. 7. A graph of response relative to control in urine (standard difference; y-axis) versus time from acetaminophen (1500 mg/kg) dosing (x-axis) for each of the 7 peaks listed in Table IV.

To determine whether the responses of the small group of 7 biochemical entities extracted from the rat liver data have potential for use as a biomarker of liver toxicity in a target tissue, such as serum or urine, the relative response of the 7 entities was analyzed in the biochemical profiling data for the rat serum and urine collected along with the liver data in the study described in Example 1. Upon analysis, 6 of the 7 liver entities were both present in serum and urine, and shown to have responses that varied significantly in the urine and serum samples. The 6 entities are aspartic acid, Peak12, glutamine, Peak20, succinic acid, and Peak26. Peak13 was not observed in serum and the response for Peak13 in urine did not vary significantly from control (FIG. 7).

Specifically, the forgoing 6 peak responses met the following criteria established for a potential biomarker: i) the peak responses were among those rated most highly by the SDA, ii) each of the peak responses varied significantly from baseline in the rat liver subset, and iii) because the liver subset was not the target tissue dataset, each of the peak responses in the subset was detectable in the target tissue (i.e. serum and urine in the present case) and varied significantly from the baseline in the target tissue datasets.

Having met the criteria for a potential biomarker of liver toxicity in serum and urine, the small group of 6 data points was subjected to parametric discriminant analysis to obtain a discrimination score that measures how well the small group distinguishes between the experimental groups of the target dataset, wherein a high discrimination score indicates the small group as a putative biomarker of the trend of interest in the target tissue. A discrimination score of 100% led to the hypothesis that the relative response of compounds corresponding to the 6 peaks present in serum and urine is potentially useful as a biomarker for acetaminophen hepatotoxicity, as the responses are associated with the toxic effects of acetaminophen on liver but detectable in the target tissues, serum and urine.

Example 6

Data Analysis Methods: Locating a Subset of Gene Expression Data of Most Interest that Corresponds to an Observed Trend A list of relative responses for annotated genes is produced for the liver samples subjected to gene expression profiling via microarray analysis as described in Example 1. The resulting dataset consists of probes (subsets of genes) and corresponding expression levels. PCA is performed on the gene expression data. Similar to that described in Example 2, mathematical models of the trends observed in the PCA plot can be developed and each of the relative response data points in the liver gene expression profiling dataset tested for adherence to the mathematical models to locate the subset of genes that follows the observed trends. The genes that adhere to the model are identified as the subset of most interest for further analysis of acetaminophen-induced liver changes. To further investigate the mode of action of acetaminophen, the genes in the identified subset are mapped to metabolic pathways. In this manner, hypotheses can be generated about the mode of action of acetaminophen toxicity.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for locating a subset within an experimental set of biological data points that is of most interest for further analysis, the method comprising:
   a) obtaining a set of data points associated with a biological phenomenon of interest, wherein the set of data points comprises a baseline and one or more experimental groups;
   b) designating a trend of interest in the set of data points that is associated with the biological phenomenon of interest, wherein the trend indicates a relationship between the data points and an independent variable;
   c) developing a mathematical model of the trend, the mathematical model being a function of the independent variable and wherein the mathematical model models the trend with respect to the independent variable;
   d) testing each data point in the set for adherence to the mathematical model, wherein the data points adhering to the model are identified as being members of the subset of most interest for further analysis; and
   e) providing identification of the members of the subset in a user-readable format,
wherein all of the steps b), c), d), and e) are performed on a suitably-programmed computer.

2. The method of claim 1 wherein the designated trend of interest is not evident in the set of data points as a whole.

3. The method of claim 2 wherein the designated trend of interest is one previously observed for the biological phenomenon of interest.

4. The method of claim 2 wherein the designated trend of interest is one that is expected for the biological phenomenon of interest.

5. The method of claim 1 wherein the set of data points is selected from the group consisting of biochemical profiling data, gene expression profiling data, protein expression profiling data, and tissue feature data.

6. The method of claim 1 wherein the set of data point are biochemical profiling data points and the biological phenomenon of interest is liver toxicity.

7. A method for investigating the molecular mode of action of a biological phenomenon of interest, the method comprising:
   a) obtaining a set of data points associated with a biological phenomenon of interest using biochemical profiling, gene expression profiling, or protein expression profiling, wherein the set of data points comprises a baseline and one or more experimental groups;
   b) designating a trend of interest in the set of data points that is associated with the biological phenomenon of interest, wherein the trend indicates a relationship between the data points and an independent variable;
   c) developing a mathematical model of the trend, the mathematical model being a function of the independent variable and wherein the mathematical model models the trend with respect to the independent variable;
   d) testing each data point in the set for adherence to the mathematical model;
   e) identifying, from a plurality of possible metabolic pathways, one or more metabolic pathways to which the data points that adhere to the model belong, wherein the mode of action of the phenomenon of interest affects the identified metabolic pathways; and
   f) providing identification of the identified metabolic pathways in a user-readable format,
wherein all of the steps b), c), d), e), and f) are performed on a suitably-programmed computer.

8. The method of claim 7 wherein the designated trend of interest is not evident in the set of data points as a whole.

9. The method of claim 8 wherein the designated trend of interest is one previously observed for the biological phenomenon of interest.

10. The method of claim 8 wherein the designated trend of interest is one that is expected for the biological phenomenon of interest.

11. The method of claim 7 wherein the set of data points is obtained using biochemical profiling and the biological phenomenon of interest is liver toxicity.

12. The method of claim 1 wherein designating a trend relative to an independent variable comprises designating a trend relative to at least one of time and an input variable.

13. The method of claim 12 wherein the input variable comprises an amount of exposure to or dose of a chemical entity.

14. The method of claim 1 wherein developing a mathematical model of the trend comprises modeling the trend as a linear or quadratic function.

15. The method of claim 7 wherein designating a trend relative to an independent variable comprises designating a trend relative to at least one of time and an input variable.

16. The method of claim 15 wherein the input variable comprises an amount of exposure to or dose of a chemical entity.

17. The method of claim 7 wherein developing a mathematical model of the trend comprises modeling the trend as a linear or quadratic function.

* * * * *